United States Patent
Muto et al.

(10) Patent No.: US 9,955,866 B2
(45) Date of Patent: May 1, 2018

(54) OPTICAL TOMOGRAPHIC IMAGING APPARATUS

(71) Applicant: CANON KABUSHIKI KAISHA, Tokyo (JP)

(72) Inventors: Kenji Muto, Fujisawa (JP); Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days. days.

(21) Appl. No.: 15/212,517

(22) Filed: Jul. 18, 2016

(65) Prior Publication Data

US 2016/0324417 A1 Nov. 10, 2016

Related U.S. Application Data

(63) Continuation of application No. 14/263,831, filed on Apr. 28, 2014, now Pat. No. 9,427,150.

(30) Foreign Application Priority Data

Apr. 30, 2013 (JP) .................................. 2013-095624

(51) Int. Cl.
*A61B 3/14* (2006.01)
*A61B 3/10* (2006.01)
*A61B 3/117* (2006.01)
*A61B 3/12* (2006.01)
*G02B 27/14* (2006.01)

(52) U.S. Cl.
CPC ............ *A61B 3/102* (2013.01); *A61B 3/1025* (2013.01); *A61B 3/117* (2013.01); *A61B 3/12* (2013.01); *G02B 27/141* (2013.01)

(58) Field of Classification Search
CPC .. A61B 3/102; A61B 3/14; A61B 3/12; A61B 3/0008; A61B 2090/3735
USPC .......................... 351/206, 205, 246, 221, 208
See application file for complete search history.

(56) References Cited

U.S. PATENT DOCUMENTS

| 8,939,583 B2 * | 1/2015 | Borycki | A61B 3/102 351/208 |
| 2014/0211155 A1 * | 7/2014 | Sakagawa | A61B 3/113 351/206 |

* cited by examiner

*Primary Examiner* — Hung Dang
(74) *Attorney, Agent, or Firm* — Canon U.S.A., Inc. IP Division

(57) ABSTRACT

An optical tomographic imaging apparatus includes a first lens having a first focal length, a second lens having a second focal length longer that the first focal length, a scanning unit disposed at a focal position of the second lens, and an optical path branching unit disposed between the first and second lenses. An observation optical path located on a transmission optical path of the optical path branching unit, and an optical path of measurement light located on a reflection optical path of the optical path branching unit. The second lens is disposed on the optical path of the measurement light between the first lens and the scanning unit, such that an angle at which the measurement light scanned by the scanning unit is incident on the optical path branching unit is maintained substantially unchanged during scanning.

22 Claims, 7 Drawing Sheets

FIG. 6A

| | (1) | (2) | (3) | (4) | (5) | (6) |
|---|---|---|---|---|---|---|
| A | ANTERIOR EYE OBSERVATION | | FUNDUS OBSERVATION | | | |
| B (103 REFLECTION) | FUNDUS OBSERVATION | OCT | ANTERIOR EYE OBSERVATION | OCT | ANTERIOR EYE OBSERVATION | FUNDUS OBSERVATION |
| C (103 TRANSMISSION) | OCT | FUNDUS OBSERVATION | OCT | ANTERIOR EYE OBSERVATION | FUNDUS OBSERVATION | ANTERIOR EYE OBSERVATION |

FIG. 6B

| | (7) | (8) | (9) | (10) | (11) | (12) |
|---|---|---|---|---|---|---|
| A' | ANTERIOR EYE OBSERVATION | | FUNDUS OBSERVATION | | | |
| B' (103 REFLECTION) | FUNDUS OBSERVATION | OCT | ANTERIOR EYE OBSERVATION | OCT | ANTERIOR EYE OBSERVATION | FUNDUS OBSERVATION |
| C' (103 TRANSMISSION) | OCT | FUNDUS OBSERVATION | OCT | ANTERIOR EYE OBSERVATION | FUNDUS OBSERVATION | ANTERIOR EYE OBSERVATION |

OPTICAL TOMOGRAPHIC IMAGING APPARATUS

CROSS-REFERENCE TO RELATED APPLICATIONS

This application is a Continuation of co-pending U.S. patent application Ser. No. 14/263,831, filed Apr. 28, 2014, now U.S. Pat. No. 9,427,150, which claims foreign priority benefit of Japanese Patent Application No. 2013-095624 filed Apr. 30, 2013. The above-named patent applications are hereby incorporated by reference herein in theft entirety.

BACKGROUND OF THE INVENTION

Field of the Invention

The present invention relates to an optical tomographic imaging apparatus for use in an ophthalmologic medical care and the like.

Description of the Related Art

Currently, various ophthalmologic apparatuses using optical apparatuses are known. For example, various apparatuses such as an anterior eye portion imaging apparatus, a fundus camera, and a confocal scanning laser ophthalmoscope (SLO) are used as optical apparatuses for observing a subject's eye. Among them, an optical tomographic imaging apparatus based on optical coherence tomography (OCT) utilizing multi-wavelength lightwave interference is an apparatus that can acquire a tomographic image of a sample at a high resolution, and is becoming an apparatus essential for clinics specialized in retinas as an ophthalmologic apparatus. Hereinafter, this apparatus will be referred to as an OCT apparatus.

The OCT apparatus emits measurement light, which is low-coherent light, to the sample, and can measure backscattering light from this sample at a high sensitivity by using an interference system or an interference optical system. The low-coherent light is characterized in that a tomographic image can be acquired at a high resolution by increasing a wavelength width thereof. Further, the OCT apparatus can acquire a tomographic image at a high resolution by scanning the measurement light on the sample. Therefore, the OCT apparatus can acquire a tomographic image of a retina on a fundus of a subject's eye (sample), and is widely used in an ophthalmologic diagnosis and the like of a retina.

Generally, the OCT apparatus as an ophthalmologic apparatus includes a fundus observation optical system, an anterior eye observation optical system, and the like for an alignment adjustment between the apparatus and the subject's eye. The OCT apparatus is constructed by using light beams having different wavelengths in the respective optical systems and separating the wavelengths with use of a wavelength separation unit such as a dichroic mirror, to allow the OCT apparatus to be used together with these optical systems.

Now, suppose that a light source for OCT emits light having a central wavelength of 855 nm, and a wavelength band from approximately 805 nm to approximately 905 nm with a wavelength bandwidth of approximately 100 nm. On the other hand, a light source for OCT discussed in Japanese Patent Application Laid-Open No. 2011-11052 emits light having a central wavelength of 840 nm, and a wavelength band from approximately 815 nm to approximately 865 nm with a wavelength bandwidth of approximately 50 nm. Further, suppose that a light source configured to generate light having a wavelength of 780 nm is used as a light source of an SLO. In this case, an interval between the wavelength of the light source of the SLO and an end of the wavelength band of the light source for OCT is approximately 35 nm (815 nm-780 nm) in the technique discussed in Japanese Patent Application Laid-Open No. 2011-11052. On the other hand, in the case where the wavelength bandwidth is approximately 100 nm, this interval is approximately 25 nm (805 nm-780 nm). In this manner, in the case of the wavelength bandwidth of approximately 100 nm, the wavelength bandwidth of the light source for OCT is wider than that of the technique discussed in Japanese Patent Application Laid-Open No. 2011-11052, thereby leading to a reduction in the interval between the wavelength of the light source of the SLO and the end of the wavelength band of the light source for OCT.

SUMMARY OF THE INVENTION

According to an aspect of the present invention, an optical tomographic imaging apparatus, which is configured to acquire a tomographic image of an object to be examined based on light generated by combining return light from the object to be examined irradiated by measurement light via a first lens and reference light corresponding to the measurement light, includes a scanning unit disposed on an optical path of the measurement light and configured to scan the measurement light on the object to be examined, a second lens disposed on the optical path of the measurement light between the scanning unit and the first lens, and an optical path branching unit disposed between the first lens and the second lens and configured to branch the optical path of the measurement light to form an observation optical path for observing the object to be examined therefrom. The observation optical path is located on a transmission optical path of the optical path branching unit. The optical path of the measurement light is located on a reflection optical path of the optical path branching unit. The second lens and the scanning unit are disposed in a manner such that an angle at which the measurement light scanned by the scanning unit is incident on the optical path branching unit is maintained substantially unchanged during scanning.

Further features of the present invention will become apparent from the following description of exemplary embodiments with reference to the attached drawings.

BRIEF DESCRIPTION OF THE DRAWINGS

FIGS. 6A and 6B are exemplary tables that indicate how respective optical systems are arranged according to the second exemplary embodiment.

DESCRIPTION OF THE EMBODIMENTS

A change in an incident angle of measurement light to a dichroic mirror typically leads to a change in a wavelength separation characteristic (a wavelength band of light transmittable through the dichroic mirror). Therefore, if a low-coherent light source configured to emit light having a wider wavelength bandwidth than that of a conventional technique is used as a light source for OCT, the accuracy for wavelength separation should be further improved compared to the conventional technique because of a shorter interval between a wavelength of a light source of an SLO and an end of the wavelength band of the light source for OCT.

According to exemplary embodiments of the present invention, an optical tomographic imaging apparatus includes a scanning unit disposed on an optical path of measurement light with which an object to be examined is irradiated via a first lens, and a second lens disposed between the scanning unit and the first lens. Then, the second lens and the scanning unit are disposed in such a manner that an angle at which the measurement light scanned by the scanning unit is incident on an optical path branching unit is substantially maintained. For example, the scanning unit is disposed at a substantially focal position of the second lens. As a result, even when the measurement light is scanned by the scanning unit, it is possible to reduce a change in a wavelength separation characteristic of the optical path branching unit. Therefore, even if a low-coherent light source configured to emit light having a wider wavelength bandwidth than that of the conventional technique is used as the light source for OCT, it is possible to improve the accuracy of wavelength separation for separating the wavelength of the light source for OCT and the wavelength of the light source of the SLO. For example, it is possible to reduce a variation in a transmittance (or a reflectance) of a predetermined wavelength to be separated by the dichroic mirror, which occurs due to a difference in the angle at which the measurement light is incident on the dichroic mirror. The wavelength separation characteristic refers, for example, to a ratio between wavelength transmission to wavelength reflection.

Figure 5A:
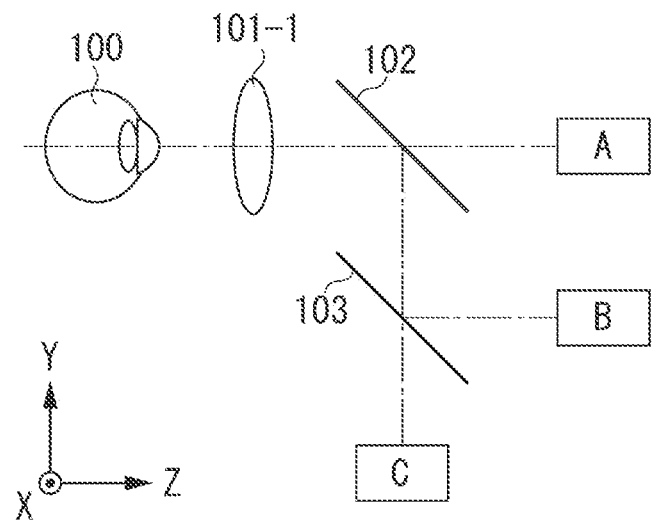
FIGS. 5A and 5B illustrate optical systems in which a second dichroic mirror 103 is disposed on different optical paths according to a second exemplary embodiment.
Figure 5B:
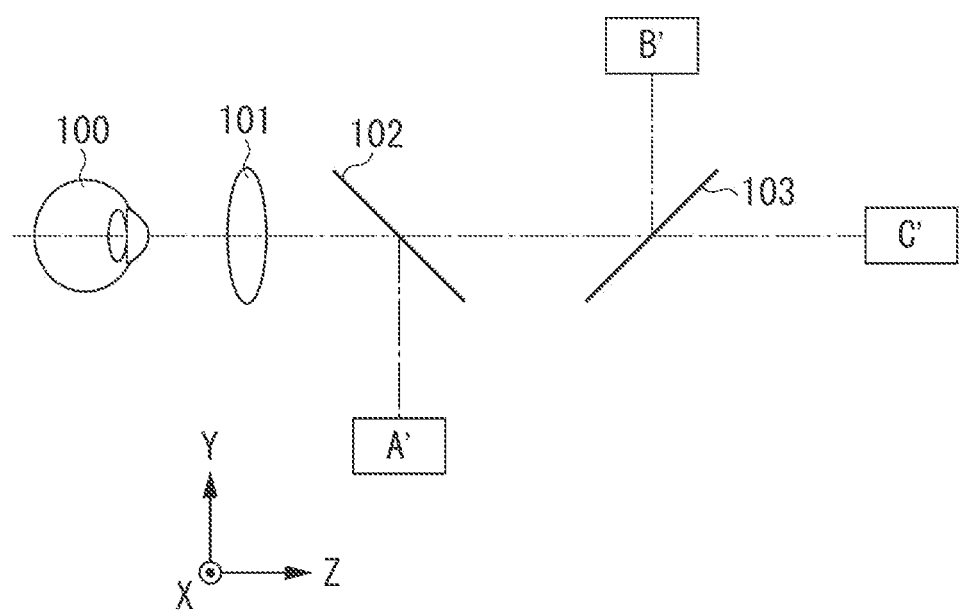

Now, as illustrated in FIGS. 6A and 6B, there are at least twelve ways to arrange optical systems depending on which optical paths an anterior eye observation optical system, a fundus observation optical system, and an OCT optical system are disposed, respectively. FIGS. 6A and 6B are tables that indicate how the respective optical systems are arranged. An optical path desirable for the anterior eye observation optical system, and an optical path desirable for the fundus observation optical system will be described with reference to FIGS. 5A and 5B. FIGS. 5A and 5B illustrate optical systems in which a second dichroic mirror 103 is disposed on different optical paths. The respective arrangements and features thereof will be described in detail in a description of a second exemplary embodiment with reference to FIGS. 5A and 5B, and FIGS. 6A and 6B.

<Optical Path Desirable for Anterior Eye Observation Optical System>

First, an optical path desirable for the anterior eye observation optical system will be described.

The fundus observation optical system and the OCT optical system are configured in such a manner that return light generated by a return of the measurement light scanned by the scanning unit from a subject's eye is incident on the second lens with an angle of approximately 45 degrees via the dichroic mirror. On the other hand, in the anterior eye observation optical system, light from an anterior eye portion of the subject's eye enters a fourth lens (for example, a lens 141 illustrated in FIG. 1), which is a lens of the anterior eye portion optical system, while being scattered via the dichroic mirror. Therefore, in the anterior eye portion optical system, as the distance from the first lens (for example, a lens 101-1 illustrated in FIG. 1) to the fourth lens increases, the light is scattered more widely, thereby leading to an increase in size of the fourth lens. Constructing a relay lens to reduce the scattering results in an increase in the number of optical members, thereby leading to an increase in the size of the anterior eye observation optical system.

For this reason, it is desirable that the anterior eye observation optical system is disposed on an optical path close to the first lens. For example, it is desirable that, in FIG. 5A, the anterior eye observation optical system is disposed on an optical path A (a transmission optical path of a first dichroic mirror 102), and in FIG. 5B, the anterior eye observation optical system is disposed on an optical path A' (a reflection optical path of the first dichroic mirror 102).

<Optical Path Desirable for Fundus Observation Optical System>

Next, an optical path desirable for the fundus observation optical system will be described.

First, it is desirable that the measurement light for the SLO in the fundus observation optical system has a larger beam diameter when the measurement light is incident on the anterior eye portion, than the measurement light for OCT in the OCT optical system. The reason for the difference in diameter is as follows. In the SLO optical system, the return light from the subject's eye is detected by a single detector 116 after being formed into a ring shape by a prism 118 such as a holed mirror. In the SLO optical system, a light amount reduces according to the formation of the return light into a ring shape. Therefore, it is desirable to increase the beam diameter as much as possible. On the other hand, the OCT optical system acquires a tomographic image with use of interference light at a position close to a coherence gate. Therefore, when a tomographic image of a fundus is captured, the tomographic image does not contain an image of normal reflection on the anterior eye portion away from a range where the tomographic image is acquired. Therefore, the return light from the subject's eye does not have to be formed into a ring shape in the OCT optical system, unlike the SLO optical system, whereby the measurement light for OCT can have a smaller beam diameter than the measurement light for the SLO. The SLO optical system may be configured to form the measurement light before application to the subject's eye into a ring shape.

In this case, as the beam diameter increases, a range where the lens is irradiated with the beam increases in a radial direction of the lens, whereby the beam is scattered more widely. Therefore, the measurement light for the SLO is more largely affected by an astigmatism on a transmission optical path of the dichroic mirror than the measurement light for OCT. For this reason, it is desirable that the fundus observation optical system is disposed on a reflection optical path of the dichroic mirror. For example, it is desirable that, in FIG. 5A, the fundus observation optical system is disposed on an optical path B (a reflection optical path of the first dichroic mirror 102 and a reflection optical path of the second dichroic mirror 103), and in FIG. 5B, the fundus observation optical system is disposed on the optical path A' (the reflection optical path of the first dichroic mirror 102).

However, as illustrated in FIG. 5B, if the first dichroic mirror 102 and the second dichroic mirror 103 are disposed so at an angle of approximately 90 degrees relative to each other, astigmatisms that occur on the respective mirrors can be canceled out even on an optical path C', which is a transmission optical paths of the two dichroic mirrors. Therefore, in FIG. 5B, it is also desirable that the fundus observation optical system is disposed on the optical path C'. Of course, one of the first dichroic mirror 102 and the second dichroic mirror 103 may be disposed at a position in which the one has rotated by approximately 90 degrees around an optical axis relative to the other. As a result, it is possible to reduce an astigmatism as a whole by generating astigmatisms on the first dichroic mirror 102 and the second dichroic mirror 103.

Figure 1:
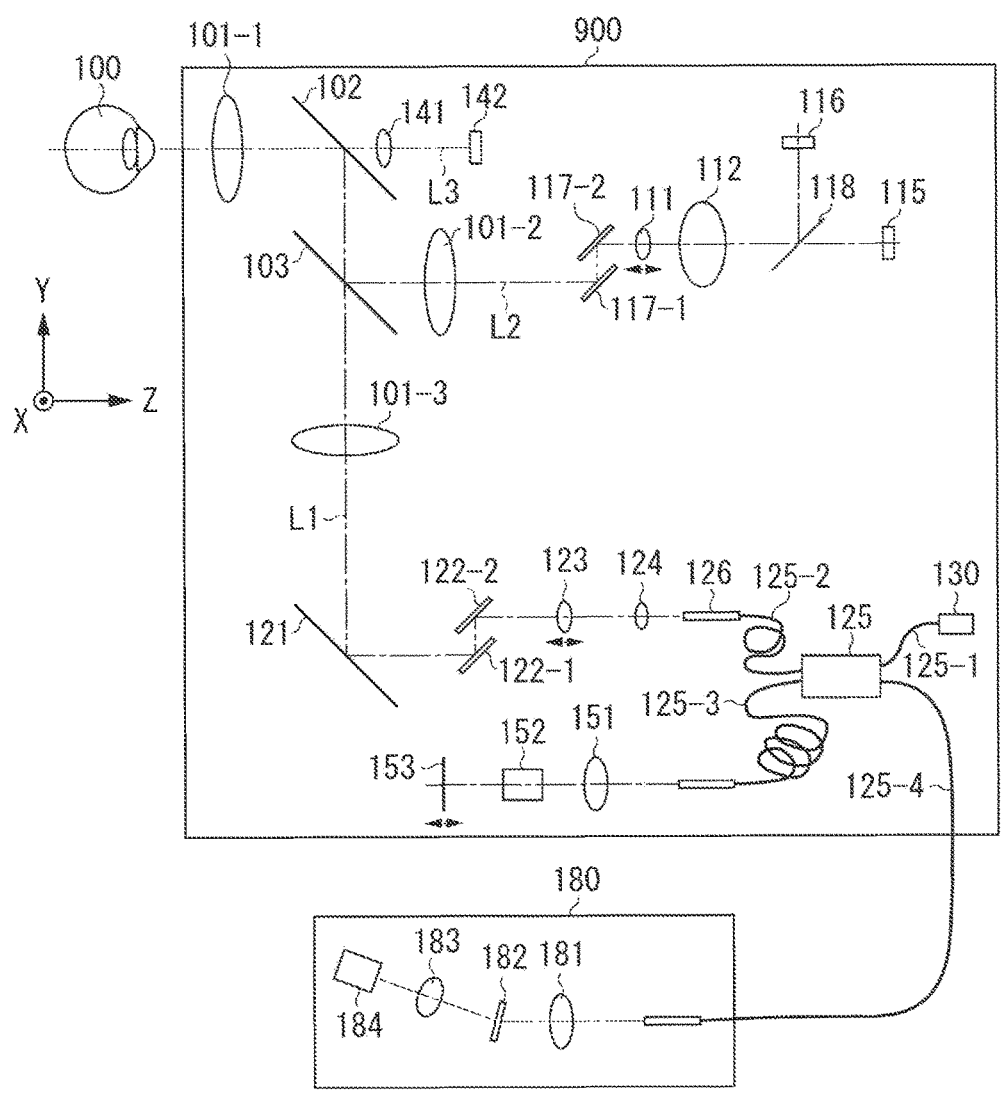
FIG. 1 illustrates an outline of a configuration of an optical tomographic imaging apparatus according to a first exemplary embodiment.

In this manner, in FIG. 5A, it is desirable that the anterior eye observation optical system, the fundus observation optical system, and the OCT optical system are disposed on the optical path A, the optical path B, and the optical path C, respectively, i.e., they are arranged as illustrated in FIG. 1. Further, in FIG. 5B, it is desirable that the anterior eye observation optical system, the fundus observation optical system, and the OCT optical system are disposed on the optical path A', the optical path C', and the optical path B', respectively.

First Exemplary Embodiment: Optical System in which Second Optical Path Branching Unit is Disposed on Reflection Optical Path of First Optical Path Branching Unit In the following description, a first exemplary embodiment of the present invention will be described with reference to the accompanying drawings. The same elements are identified with the same reference numerals throughout the present disclosure.

<Configuration of Apparatus>

A configuration of the optical tomographic imaging apparatus (OCT apparatus) according to the present exemplary embodiment will be described with reference to FIG. 1. The optical tomographic imaging apparatus includes an optical head 900 and a spectrometer 180. The optical tomographic imaging apparatus acquires a tomographic image of the object to be examined based on light generated by combining the return light from the object to be examined irradiated by the measurement via the scanning unit, and reference light corresponding to this measurement light.

First, an internal configuration of the optical head 900 will be described. The optical head 900 includes an OCT optical system for capturing an image of an anterior eye of a subject's eye 100, a two-dimensional image of a fundus of the subject's eye 100, and a tomographic image of the subject's eye 100. The lens 101-1, which is an objective lens and an example of the first lens, is disposed so as to face the subject's eye 100. Further, an optical path is branched by the first dichroic mirror 102 and the second dichroic mirror 103, which are the optical path branching unit. More specifically, the optical path is branched into a measurement optical path L1 of the OCT optical system, a fundus observation optical path and fixation lamp optical path L2, and an anterior eye portion observation optical path L3 according to each wavelength band.

<Optical Path L1: Measurement Optical Path of Oct Optical System>

The optical path L1 is the measurement optical path of the OCT optical system, which is separated according to wavelength from the light of the anterior eye observation optical system on the optical path L3 by the first dichroic mirror 102, and is further separated according to the wavelength from the measurement light of the fundus observation optical system on the optical path L2 by the second dichroic mirror 103. The OCT optical system is used to capture a tomographic image of the fundus of the subject's eye 100. More specifically, the optical path L1 is used to acquire an interference signal for forming a tomographic image. A lens 101-3, which is an example of the second lens, a mirror 121, and the scanning unit are disposed on the optical path L1. The scanning unit includes an X scanner 122-1, which is an example of a first scanning unit, and a Y scanner 122-2, which is an example of a second scanning unit. A non-limiting example of the X scanner 122-1 and Y scanner 122-2 includes a scanning galvanometer. One-dimensional (1D) or two-dimensional (2D) galvanometer optical scanners may be used. Other non-limiting examples may include 1D or 2D MEMS (micro-electromechanical mirrors) scanning mirrors. Regardless of the implementation, the X scanner 122-1 and the Y scanner 122-2 scan the light on the fundus of the subject's eye 100 in an X direction (a main scanning direction), which is an example of a first direction, and a Y direction (a sub scanning direction), which is an example of a second direction intersecting with the first direction. In FIG. 1, an optical path between the X scanner 122-1 and the Y scanner 122-2 is formed in a direction in parallel with the plane of the sheet of FIG. 1, but actually, this optical path is formed in a direction perpendicularly to the plane of the sheet of FIG. 1.

<Optical Path L2: Optical Path of Fundus Observation Optical System>

The optical path L2 is the optical path of the fundus observation optical system, which is separated according to the wavelength from the measurement light of the OCT optical system on the optical path L1 by the second dichroic mirror 103. Among a lens 101-2, a focusing lens 111, and a lens 112, the focusing lens 111 is driven by a motor (not-illustrated) for a focusing adjustment for a fixation lamp and fundus observation (not-illustrated).

First, on the optical path L2, a light source 115 (the light source of the SLO) for fundus observation generates light having a wavelength of 780 nm. Further, an X scanner 117-1, which is an example of a first observation scanning unit, and a Y scanner 117-2, which is an example of a second observation scanning unit, are disposed on the optical path L2 to scan the light emitted from the light source 115 for fundus observation on the fundus of the subject's eye 100. The lens 101-2, which is an example of a third lens, is disposed so as to have a focal position around a central position between the X scanner 117-1 and the Y scanner 117-2. The X scanner 117-1 includes a polygon mirror to scan the light in the X direction at a high speed. Further, the X scanner 117-1 may include a resonant mirror. Further, the single detector 116 includes an avalanche photodiode (APD), and detects the light scattered by and reflected from the fundus. The prism 118 is a prism to which a holed mirror or a hollow mirror is evaporated, and separates the illumination light from the light source 115 for fundus observation and the return light from the fundus.

Further, a dichroic mirror (not-illustrated) may be further provided, and a light-emitting diode (LED) or the like may be further provided as a light source of the fixation lamp (not-illustrated). In this case, the light source of the fixation lamp is disposed on the SLO light source side relative to the scanning unit for observation. Due to this arrangement, the scanning unit for observation is also used as a scanning unit for visual fixation, by which a scanning fixation lamp can be formed. In this case, this scanning fixation lamp can work well by using a control unit (not-illustrated) that performs control in such a manner that the light source of the fixation lamp is turned on when light from the light source of the fixation lamp is scanned at a position desired by an examiner. Turning on and turning off the light source of the fixation lamp may be replaced with opening and closing a shutter disposed on this optical path.

The optical path L2 may be a line scanning SLO (a line SLO) that scans a line beam in a single direction by using a cylindrical lens or the like, instead of the above-described point scanning SLO that two-dimensionally scans a spot to acquire a two-dimensional image of the fundus. Further, the optical path L2 may be configured to perform infrared observation by using a two-dimensional charge coupled device (CCD) sensor, instead of using the scanning unit. More specifically, the optical path L2 may be configured to include a CCD sensor for fundus observation, instead of the X scanner 117-1 and the Y scanner 117-2, to acquire a two-dimensional image of the fundus of the subject's eye 100. In this case, the two-dimensional CCD sensor has a sensitivity to a wavelength of the illumination light (not-illustrated) for fundus observation, in particular, around 780 nm.

Further, the fixation lamp on the optical path L2 may be configured in such a manner that the examiner prompts visual fixation of an examinee to a desired position by generating visual light by a display for visual fixation such as a liquid-crystal display, and changing a lighting position on the display for visual fixation. In this case, the display for visual fixation is disposed closer to a third dichroic mirror 104 relative to the scanning unit for observation.

<Optical Path L3: Optical Path of Anterior Eye Observation Optical System>

The optical path L3 is the optical path of the anterior eye observation optical system where the lens 141, and an infrared CCD sensor 142 for anterior eye observation are disposed. The infrared CCD sensor 142 has sensitivity to wavelength of the illumination light (not-illustrated) for anterior eye observation, in particular, around 970 nm.

<Position Optically Conjugate with Anterior Eye Portion: Substantially Central Position Between X and Y Scanners Coincides with Focal Position of Lens>

Now, conjugate relationships between the eye position and the optical path L1 and the optical path L2, and a light flux of the eye will be described with reference to FIG. 2. The optical tomographic imaging apparatus is configured in such a manner that a position conjugate with a predetermined portion such as the anterior eye portion of the subject's eye 100 is located between the first scanning unit and the second scanning unit. The present exemplary embodiment can be realized as long as at least one of the optical path L1 and the optical path L2 is configured in this manner.

First, on the optical path L1, a scanner central position 127 between the X scanner 122-1 and the Y scanner 122-2, and a pupil position 128 (the anterior eye portion) of the subject's eye 100 are in an optically conjugate relationship. More specifically, the optical system of the optical head 900 is designed in such a manner that the X and Y scanners 122-1 and 122-2 configured to scan the measurement light for OCT in the X and Y directions and the anterior eye portion are set in an optically conjugate relationship, when the optical head 900 and the subject's eye 100 are aligned with each other. As a result, it is possible to reduce vignetting of the measurement light on the anterior eye portion of the subject's eye 100.

Further, the lens 101-1, the lens 101-3, and the X scanner 122-1 and the Y scanner 122-2 (or the scanner central position 127) are disposed in such a manner that a light flux of the measurement light scanned by the scanning unit is substantially collimated between the lens 101-1 and the lens 101-3. According to this configuration, an optical path for which a measurement light deflection unit is set as an object point is substantially collimated between the lens 101-1 and the lens 101-3. Then, the scanner central position 127 coincides with a focal position of the lens 101-3. Due to this configuration, it is possible to substantially maintain angles at which the measurement light is incident on the first dichroic mirror 102 and the second dichroic mirror 103, even when the X scanner 122-1 and the Y scanner 122-2 scan the measurement light. That is, the second lens 101-3 and the scanning unit (scanner 122-1 and scanner 122-2) are disposed in such a manner that an angle at which the measurement light scanned by the scanning unit is incident on the optical path branching unit is maintained substantially unchanged during scanning of subject's eye. As a result, even when the measurement light for OCT is scanned by the X and Y scanners 122-1 and 122-2, it is possible to reduce changes in the wavelength separation characteristics of the dichroic mirrors 102 and 103, whereby it is possible to improve the accuracy of wavelength separation by the dichroic mirrors 102 and 103.

Further, on the optical path L2, a scanner central position 119 between the X scanner 117-1 and the Y scanner 117-2, and the pupil position 128 of the subject's eye 100 are also in a conjugate relationship. Further, the lens 101-2 and the scanner central position 119 (the X scanner 117-1 and the Y scanner 117-1) are disposed in such a manner that a light flux is substantially collimated between the lens 101-1 and the lens 101-2. According to this configuration, an optical path for which a measurement light deflection unit is set as an object point is substantially collimated between the lens 101-1 and the lens 101-2. Then, the scanner central position 119 coincides with a focal position of the lens 101-2. Due to this configuration, it is possible to substantially maintain angles at which the measurement light is incident on the first dichroic mirror 102 and the second dichroic mirror 103, even when the X scanner 117-1 and the Y scanner 117-2 scan the measurement light. As a result, even when the measurement light for the SLO is scanned by the X and Y scanners 117-1 and 117-2, it is possible to reduce changes in the wavelength separation characteristics of the dichroic mirrors 102 and 103, whereby it is possible to improve the accuracy of wavelength separation by the dichroic mirrors 102 and 103.

Further, the optical path L1 and the optical path L2 are configured to share the lens 101-1, and it is desirable that the lens 101-2 and the lens 101-3 are configured by lenses having similar shapes and made of similar materials. As a result, it is possible to establish matching optical systems from the subject's eye 100 to the respective X and Y scanners 122-1, 122-2, 117-1, and 117-2 on the optical path L1 and the optical path L2, whereby it is possible to uniform optical characteristics on the optical paths L1 and L2. Therefore, it becomes possible to reduce an error in a measurement.

Figure 2:
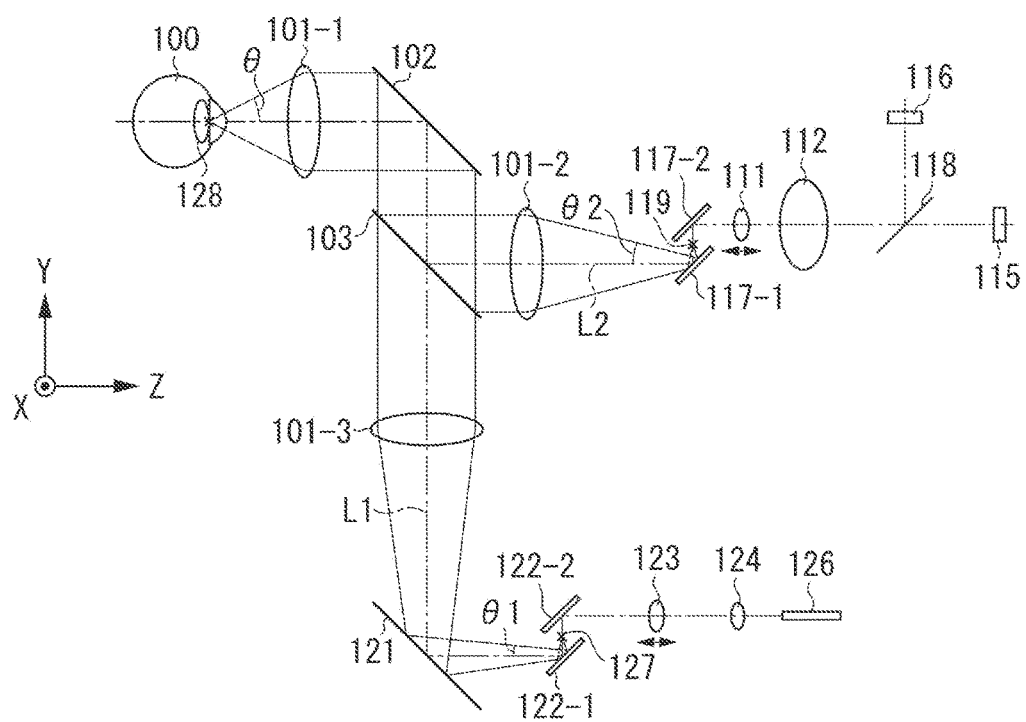
FIG. 2 illustrates exemplary optical paths of a light flux incident on a pupil of a subject's eye, in an optical tomographic imaging apparatus according to the first exemplary embodiment.

Now, as illustrated in FIG. 2, assume that $\theta$ represents an angle formed by the light flux of light incident on the pupil of the subject's eye 100, $\theta 1$ represents an angle formed by the light flux of light incident on the scanner central position 127, and $\theta 2$ represents an angle formed by the light flux of light incident on the scanner central position 119. In other words, the optical tomographic imaging apparatus is configured to provide the angles θ1 and θ2 to the light beams with use of the scanners respectively to acquire the angle θ formed by the light flux of the pupil on both the optical path L1 and the optical path 12.

Further, as one of the optical characteristics, an optical magnification of the scanner central position 119 to the pupil position 128 and an optical magnification of the scanner central position 127 to the pupil position 128 can be made uniform on the optical path L1 and the optical path L2. As a result, relationships between scan angles of the X and Y scanners 122-1, 122-2, 117-1, and 117-2 on the respective optical paths L1 and L2, and illumination positions on the fundus of the subject's eye 100 can be made uniform on the optical paths L1 and L2. Therefore, the angles θ1 and θ2 can be made equal to each other. Due to this arrangement, it becomes possible to reduce an error between the respective scanning positions.

<Position Optically Conjugate with Fundus: Focusing Adjustment>

Further, the optical system of the optical head 900 is designed in such a manner that a fiber end 126 for introducing the measurement light to the measurement optical path and the fundus of the subject's eye 100 are set into an optically conjugate relationship by performing a focusing adjustment, when the X and Y scanners 122-1 and 122-2 and the anterior eye portion are in an optically conjugate relationship. The focusing lens 123 and a lens 124 are provided adjacent to the fiber end 126. The focusing lens 123 is driven in directions indicated by a double-headed arrow by a motor (not-illustrated) to perform a focusing adjustment. The focusing adjustment is performed by making an adjustment in such a manner that light emitted from the measurement light source 126, which is the fiber end, is imaged on the fundus. The focusing lens 123, which is an example of a focusing unit, is disposed between the measurement light source 126, and the X scanner 122-1 and the Y scanner 122-2, which are the measurement light deflection unit. This configuration eliminates the necessity of moving the larger lens 101-3 and a fiber 125-2 connected to the measurement light source 126.

Now, for example, U.S. Pat. No. 5,537,162 discusses a configuration that maintains a constant angle as an incident angle at which a beam is incident on a dichroic mirror even when the beam is scanned by placing a beam scanner on a back focal plane of a lens (lens corresponding to the lens 101-3 in the present exemplary embodiment). Further, U.S. Pat. No. 5,537,162 discusses that the beam scanner and the lens are integrally driven during execution of a focusing adjustment for a fundus of a subject's eye. In this case, the lens (the lens corresponding to the lens 101-3 in the present exemplary embodiment) with the beam scanner placed on the back focal plane thereof tends to have a large size to introduce scanning light of the beam scanner. Therefore, a driving mechanism therefor is complicated, because the beam scanner and the large-sized lens should be integrally moved. Further, since they are integrally moved, a measurement light source in an optically conjugate relationship with a fundus position should be moved at the same time. If this measurement light source is an optical fiber end, an optical fiber should be moved, whereby a change may occur in a polarized state. Therefore, according to the present exemplary embodiment, as described above, the focusing lens 123 is disposed between the X and Y scanners 122-1 and 122-2 that scan the measurement light for OCT in the X and Y directions, and the fiber end 126 that emits the measurement light for OCT (or an optical coupler 125 that branches light into the measurement light and the reference light). If the focusing position is changed by moving the lens 101-1 in an optical axis direction, this also causes a change in the optically conjugate relationship between the X and Y scanners 122-1 and 122-2 and the anterior eye portion, whereby vignetting of the measurement light may occur on an iris of the anterior eye portion and the like.

With this focusing adjustment, an image of the measurement light source 126 can be formed on the fundus of the subject's eye 100, and the return light from the fundus of the subject's eye 100 can be efficiently returned to the fiber 125-2 via the measurement light source 126. Further, a focusing adjustment can be performed with use of a focusing lens 111 on the optical path L2 in a similar manner.

<Configuration of Oct Optical System>

Next, configurations of an optical path of light emitted from a light source 130 illustrated in FIG. 1, a reference optical system, and the spectrometer 180 will be described. A Michelson interference system is formed by the light source 130, a mirror 153, a dispersion compensation glass 152, the optical coupler 125, optical fibers 125-1 to 125-4, a lens 151, and the spectrometer 180. The optical fibers 125-1 to 125-4 form a single-mode optical fiber by being connected to the optical coupler 125 to be integrated all together.

The light emitted from the light source 130 is transmitted to the optical coupler 125 via the optical fiber 125-1, and is divided into the measurement light emitted to the optical fiber 125-2 and the reference light emitted to the optical fiber 125-3 via the optical coupler 125. The fundus of the subject's eye 100 is irradiated with the measurement light, which is an observation target, via the above-described optical path of the OCT optical system, and reaches the optical coupler 125 via the same optical path by being reflected or scattered by a retina.

On the other hand, the reference light reaches the mirror 153 and is reflected thereby after being transmitted via the optical fiber 125-3, the lens 151, and the dispersion compensation glass 152 inserted to match dispersion of the measurement light and dispersion of the reference light. Then, the reference light reaches the optical coupler 125 by returning through the same optical path.

The measurement light and the reference light are combined by the optical coupler 125, thereby producing interference light. Interference occurs when an optical path length of the measurement light and an optical path length of the reference light become substantially equal. The mirror 153 is held in such a manner that its position can be adjusted in the optical axis direction by a motor (not-illustrated) and driving mechanism, and can match the optical path length of the reference light to the optical path length of the measurement light, which varies depending on the subject's eye 100. The interference light is guided to the spectrometer 180 via the optical fiber 125-4.

The spectrometer 180 includes a lens 181, a diffraction grating 182, a lens 183, and a line sensor 184. The interference light emitted from the optical fiber 125-4 is dispersed by the diffraction grating 182 after being substantially collimated via the lens 181, and is imaged on the line sensor 184 by the lens 183.

Next, the light source 130 will be described. The light source 130 is a super luminescent diode (SLD), which is a representative low-coherent light source. The central wavelength is 855 nm, and the wavelength bandwidth is approximately 100 nm. The wavelength bandwidth is an important parameter, because it affects a resolution of an acquired tomographic image in the optical axis direction. Further, the SLD is selected in the present example as the type of the light source, but the light source 130 may be any light source that can emit low-coherent light and can be also realized by amplified spontaneous emission (ASE) and the like. A suitable central wavelength is near infrared light in consideration of the fact that the optical tomographic imaging apparatus is used to measure a subject's eye. Further, it is desirable that the central wavelength is as a small wavelength as possible, because it affects a lateral resolution of an acquired tomographic image. For both reasons, 855 nm is selected as the central wavelength.

The present exemplary embodiment uses a Michelson interferometer as the interferometer, but may use a Mach-Zehnder interferometer. It is desirable to, according to a difference in light amount between the measurement light and the reference light, use a Mach-Zehnder interferometer if their light amounts are largely different and to use a Michelson interferometer if their light amounts are relatively slightly different.

<Method for Capturing Tomographic Image>

The optical tomographic imaging apparatus can capture a tomographic image of a desired portion on the fundus of the subject's eye 100 by controlling the X scanner 122-1 and the Y scanner 122-2.

Figure 3:
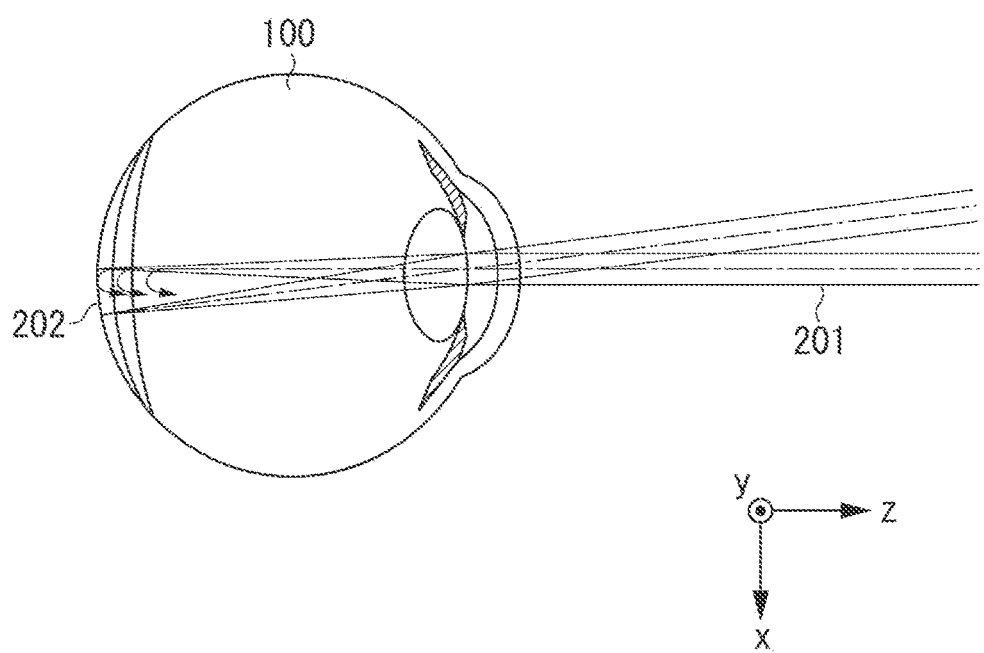
FIG. 3 illustrates an example of how measurement light is scanned on a subject's eye by an X scanner in an X direction in the optical tomographic imaging apparatus according to the first exemplary embodiment.

FIG. 3 illustrates how the subject's eye 100 is irradiated with the measurement light 201, and the measurement light 201 is scanned on a fundus 202 in the X direction. Information corresponding to a predetermined number of times of imaging is captured from an imaging range on the fundus 202 in the X direction by the line sensor 184. Luminance distribution on the line sensor 184 that is acquired at a certain position in the X direction is transformed by fast Fourier transformation (FFT). Linear luminance distribution acquired by FFT is converted into density or color information to be displayed on a monitor, and this converted image is referred to as an A-scan image. Further, a two-dimensional image formed by arranging a plurality of A-scan images is referred to as a B-scan image. A plurality of B-scan images can be acquired by capturing a plurality of A-scan images to construct a single B-scan image, and then moving a scanning position in the Y direction and performing scanning in the X direction again. The plurality of B-scan images or a three-dimensional tomographic image constructed from the plurality of B-scan images is displayed on the monitor, whereby the examiner can use the image for a diagnosis of the subject's eye 100.

Figure 4:
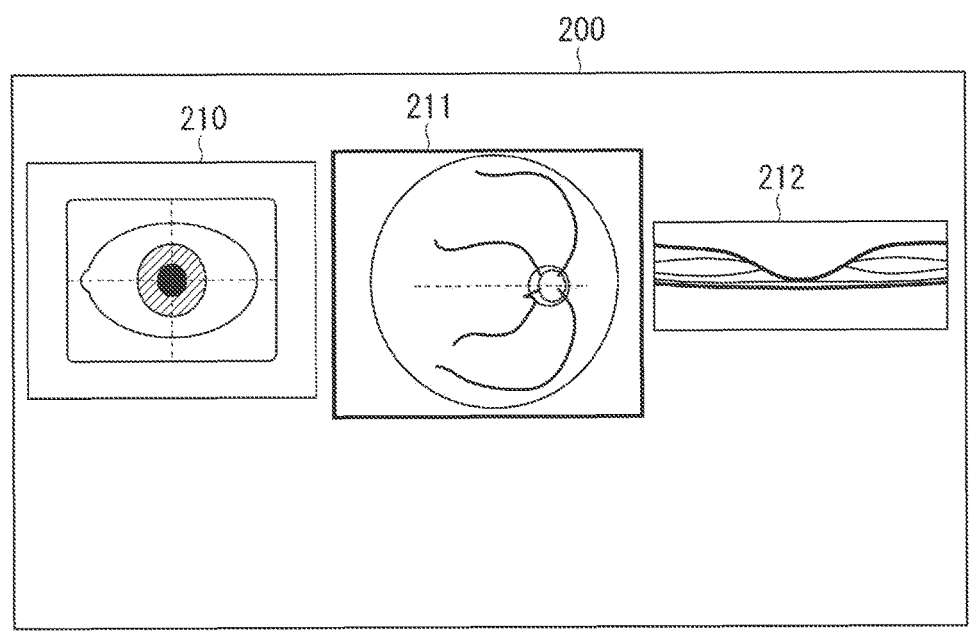
FIG. 4 illustrates exemplary representations of an image of an anterior eye, a two-dimensional image of a fundus, and a B-scan image displayed on a monitor in the optical tomographic imaging apparatus according to the first exemplary embodiment.

FIG. 4 illustrates examples of an anterior eye image 210, a fundus two-dimensional image 211, and a B-scan image 212, which is a tomographic image, displayed on a monitor 200. The anterior eye image 210 is an image processed and displayed from an output of the infrared CCD sensor 142. The fundus two-dimensional image 211 is an image processed and displayed from an output of a CCD 114. Then, the B-scan image 212 is an image constructed by performing the above-described processing from an output of the line sensor 184.

As described above, according to the present exemplary embodiment, in the optical tomographic imaging apparatus, the focusing unit (the focusing lens 123 and the driving mechanism (not-illustrated)) configured to perform a focusing adjustment that targets the subject's eye 100 is disposed between the measurement light deflection unit (the X and Y scanners 122-1 and 122-2) configured to deflect the measurement light, and the measurement light source 126. Further, the first lens (the lens 101-1) and the second lens (the lens 101-3) are disposed on the measurement optical path between the measurement light deflection unit (the X and Y scanners 122-1 and 122-2) and the subject's eye 100, and the optical path branching unit (the first dichroic mirror 102 and the second dichroic mirror 103) is disposed between the first lens and the second lens. Herein, the first dichroic mirror 102 and the second dichroic mirror 103 are non-limiting examples of an optical path branching unit. Other examples of the optical path branching unit may include a prism, a half-silvered mirror, a half-wave plate, or the like. Regardless of how the optical path branching unit is implemented, the optical path is branched into an optical path L1, and optical path L2 and an optical path L3, as shown in FIG. 1. These optical paths L1, L2 and L3 are branched according wavelength bands of the measurement light.

The focusing lens 123 is disposed between a fiber end 126 (referred to as the measurement light source) and the X and Y scanners 122-1 and 122-2 (referred to as the measurement light deflection unit). Arranging the focusing lens 123 in this manner, eliminates the necessity of moving the large lens 101-3, the fiber 125-2 connected to the measurement light source 126, and the like. Therefore, this arrangement, leads to a simplification of the driving mechanism. Further, because the fiber end 126 does not have to be moved, it is possible to provide an optical tomographic imaging apparatus capable of maintaining a polarization state substantially unchanged. Further, according to the present exemplary embodiment, in the optical tomographic imaging apparatus, the first lens (the lens 101-1) and the second lens (the lens 101-3), and the measurement light deflection unit (the X and Y scanners 122-1 and 122-2) are positionally adjusted and arranged in such a manner that the light is collimated on the measurement optical path between the first lens (the lens 101-1) and the second lens (the lens 101-3). As a result, it is possible to maintain substantially constant angles as the incident angles at which the beam is incident on the first and second dichroic mirrors 102 and 103, thereby improving the accuracy of wavelength separation.

The present exemplary embodiment has been described, targeting a subject's eye. However, the present invention may scan light on not only a subject's eye but also another object to be examined, like a human body such as skin and an internal organ, and can be employed for not only an ophthalmologic apparatus but also an imaging apparatus such as an endoscope.

Second Exemplary Embodiment: Variations of Optical System

Next, a second exemplary embodiment will be described with reference to FIGS. 5A and 5B, and FIGS. 6A and 6B. The second exemplary embodiment relates to different combinations when the anterior eye observation optical system, the fundus observation optical system, and the OCT optical system are arranged, with respect to the reflection optical path and the transmission optical path of the first dichroic mirror 102, and the reflection optical path and the transmission optical path of the second dichroic mirror 103.

FIGS. 5A and 5B illustrate the optical systems in which the second dichroic mirror 103 is disposed on the different optical paths. FIG. 5A illustrates the optical system in which the second dichroic mirror 103 is disposed on the reflection optical path of the first dichroic mirror 102. Further, FIG. 5B illustrates the optical system in which the second dichroic mirror 103 is disposed on the transmission optical path of the first dichroic mirror 102.

Further, FIGS. 6A and 6B are tables indicating several possibilities how the respective optical systems may be arranged depending on the positions of the first and second dichroic mirrors 102 and 103. FIG. 6A is a table indicating combinations in which the OCT optical system, the anterior eye observation optical system, and the fundus observation optical system are arranged with respect to the optical path A, the optical path B, and the optical path C shown in FIG. 5A. Further, FIG. 6B is a table indicating combinations in which the OCT optical system, the anterior eye observation optical system, and the fundus observation optical system are arranged with respect to the optical path A', the optical path B', and the optical path C' illustrated in FIG. 5B. A pattern (1) illustrated in FIG. 6A is a combination in which the anterior eye observation optical system, the fundus observation optical system, and the OCT optical system are disposed on the optical path A, the optical path B, and the optical path C, respectively, and this combination is a similar optical system to that of the first exemplary embodiment. Further, patterns (2) to (6) illustrated in FIG. 6A correspond to modifications of the pattern (1). In the following description, the optical system illustrated in FIG. 5A and the optical system illustrated in FIG. 5B will be described sequentially.

<Optical System Illustrated in FIG. 5a: Optical System in which Second Dichroic Mirror 103 is Disposed on Reflection Optical Path of First Dichroic Mirror 102>

Now, regarding the optical system illustrated in FIG. 5A, the patterns (1) to (6) illustrated in FIG. 6A will be described sequentially. According to the optical system illustrated in FIG. 5A, the optical head 900 can be compactly configured, because there is no another optical path than the optical path A above the optical path A.

First, in the pattern (1) illustrated in FIG. 6A, the optical path A, the optical path B, and the optical path C are the anterior eye observation optical system, the fundus observation optical system, and the OCT optical system, respectively. In this pattern, the first dichroic mirror 102 is disposed between the objective lens 101-1 and the anterior eye observation optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the fundus observation optical system on the optical path B is disposed on the reflection optical paths of the first dichroic mirror 102 and the second dichroic mirror 103. Therefore, in the fundus observation optical system, the thicknesses of the two dichroic mirrors 102 and 103 do not affect the imaging performance. As a result, it is possible to reduce astigmatism in the fundus observation optical system, whereby it is possible to acquire a fundus observation image having a high brightness and a high contrast.

Further, in the pattern (2) illustrated in FIG. 6A, the optical path A, the optical path B, and the optical path C are the anterior eye observation optical system, the OCT optical system, and the fundus observation optical system, respectively. In this pattern, the first dichroic mirror 102 is disposed between the objective lens 101-1 and the anterior eye observation optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the OCT optical system on the optical path B is disposed on the reflection optical paths of the first dichroic mirror 102 and the second dichroic mirror 103. Therefore, in the OCT optical system, the thicknesses of the two dichroic mirrors 102 and 103 do not affect the imaging performance. As a result, it is possible to reduce astigmatism in the OCT optical system, whereby it is possible to acquire a tomographic image having a high brightness and a high contrast.

Further, in the pattern (3) illustrated in FIG. 6A, the optical path A, the optical path B, and the optical path C are the fundus observation optical system, the anterior eye observation optical system, and the OCT optical system, respectively. In this pattern, the first dichroic mirror 102 is disposed between the objective lens 101-1 and the fundus observation optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the anterior eye observation optical system on the optical path B is disposed on the reflection optical paths of the first dichroic mirror 102 and the second dichroic mirror 103. Therefore, in the anterior eye observation optical system, the thicknesses of the two dichroic mirrors 102 and 103 do not affect the imaging performance. As a result, it is possible to reduce astigmatism in the anterior eye observation optical system, whereby it is possible to acquire an anterior eye observation image having a high brightness and a high contrast.

Further, in the pattern (4) illustrated in FIG. 6A, the optical path A, the optical path B, and the optical path C are the fundus observation optical system, the OCT optical system, and the anterior eye observation optical system, respectively. In this pattern, the first dichroic mirror 102 is disposed between the objective lens 101-1 and the fundus observation optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the OCT optical system on the optical path B is disposed on the reflection optical paths of the first dichroic mirror 102 and the second dichroic mirror 103. Therefore, in the OCT optical system, the thicknesses of the two dichroic mirrors 102 and 103 do not affect the imaging performance. As a result, it is possible to reduce astigmatism in the OCT optical system, whereby it is possible to acquire a tomographic image having a high brightness and a high contrast.

Further, in the pattern (5) illustrated in FIG. 6A, the optical path A, the optical path B, and the optical path C are the OCT optical system, the anterior eye observation optical system, and the fundus observation optical system, respectively. In this pattern, the first dichroic mirror 102 is disposed between the objective lens 101-1 and the OCT optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the anterior eye observation optical system on the optical path B is disposed on the reflection optical paths of the first dichroic mirror 102 and the second dichroic mirror 103. Therefore, in the anterior eye observation optical system, the thicknesses of the two dichroic mirrors 102 and 103 do not affect the imaging performance. As a result, it is possible to reduce astigmatism in the anterior eye observation optical system, whereby it is possible to acquire an anterior eye observation image having a high brightness and a high contrast.

Further, in the pattern (6) illustrated in FIG. 6A, the optical path A, the optical path B, and the optical path C are the OCT optical system, the fundus observation optical system, and the anterior eye observation optical system, respectively. In this pattern, the first dichroic mirror 102 is disposed between the objective lens 101-1 and the OCT optical system on the optical path A, and the optical path A is the transmission optical path of the first dichroic mirror 102. In this case, the optical path A is an optical path formed via a single dichroic mirror without an intervention of the second dichroic mirror 103, and therefore achieves high light use efficiency compared to the optical paths B and C. Further, the fundus observation optical system on the optical path B is disposed on the reflection optical paths of the first dichroic mirror 102 and the second dichroic mirror 103. Therefore, in the fundus observation optical system, the thicknesses of the two dichroic mirrors 102 and 103 do not affect the imaging performance. As a result, it is possible to reduce astigmatism in the fundus observation optical system, whereby it is possible to acquire a fundus observation image having a high brightness and a high contrast.

<Optical System Illustrated in FIG. 5b: Optical System in which Second Dichroic Mirror 103 is Disposed on Transmission Optical Path of First Dichroic Mirror 102>

Next, regarding the optical system illustrated in FIG. 5B, patterns (7) to (12) illustrated in FIG. 6B will be described sequentially. The optical path C' in the optical system illustrated in FIG. 5B is the transmission optical paths of the two dichroic mirrors. It is desirable that the first dichroic mirror 102 and the second dichroic mirror 103 are disposed at an angle of approximately 90 degrees relative to each other. In this case, if the first dichroic mirror 102 and the second dichroic mirror 103 have substantially the same thicknesses, in a case where an optical path shift occurs on the first dichroic mirror 102, an optical path shift occurs on the second dichroic mirror 103 in a reverse direction by a substantially the same amount. Therefore, an astigmatism generated due to the thickness of the first dichroic mirror 102 can be corrected by the second dichroic mirror 103.

First, the pattern (7) illustrated in FIG. 6B is a combination in which the optical path A', the optical path B', and the optical path C' are the anterior eye observation optical system, the fundus observation optical system, and the OCT optical system, respectively. In this pattern, the first dichroic mirror 102 is disposed between the objective lens 101-1 and the anterior eye observation optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire an anterior eye observation image having a high brightness and a high contrast on the optical path A'. Further, in the OCT optical system disposed on the optical path C', it is possible to reduce an astigmatism as described above, whereby it is possible to acquire a tomographic image having a high brightness and a high contrast.

Further, the pattern (8) illustrated in FIG. 6B is a combination in which the optical path A', the optical path B', and the optical path C' are the anterior eye observation optical system, the OCT optical system, and the fundus observation optical system, respectively. In this pattern, the first dichroic mirror 102 is disposed between the objective lens 101-1 and the anterior eye observation optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire an anterior eye observation image having a high brightness and a high contrast on the optical path A'. Further, in the fundus observation optical system disposed on the optical path C', it is possible to reduce an astigmatism as described above, whereby it is possible to acquire a fundus observation image having a high brightness and a high contrast.

Further, the pattern (9) illustrated in FIG. 6B is a combination in which the optical path A', the optical path B', and the optical path C' are the fundus observation optical system, the anterior eye observation optical system, and the OCT optical system, respectively. In this pattern, the first dichroic mirror 102 is disposed between the objective lens 101-1 and the fundus observation optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire a fundus observation image having a high brightness and a high contrast on the optical path A'. Further, in the OCT optical system disposed on the optical path C', it is possible to reduce an astigmatism as described above, whereby it is possible to acquire a tomographic image having a high brightness and a high contrast.

Further, the pattern (10) illustrated in FIG. 6B is a combination in which the optical path A', the optical path B', and the optical path C' are the fundus observation optical system, the OCT optical system, and the anterior eye observation optical system, respectively. In this pattern, the first dichroic mirror 102 is disposed between the objective lens 101-1 and the fundus observation optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire a fundus observation image having a high brightness and a high contrast on the optical path A'. Further, in the anterior eye observation optical system disposed on the optical path C', it is possible to reduce an astigmatism as described above, whereby it is possible to acquire an anterior eye observation image having a high brightness and a high contrast.

Further, the pattern (11) illustrated in FIG. 6B is a combination in which the optical path A', the optical path B', and the optical path C' are the OCT optical system, the anterior eye observation optical system, and the fundus observation optical system, respectively. In this pattern, the first dichroic mirror 102 is disposed between the objective lens 101-1 and the OCT optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire a tomographic image having a high brightness and a high contrast on the optical path A'. Further, in the fundus observation optical system disposed on the optical path C', it is possible to reduce an astigmatism as described above, whereby it is possible to acquire a fundus observation image having a high brightness and a high contrast.

Further, the pattern (12) illustrated in FIG. 6B is a combination in which the optical path A', the optical path B', and the optical path C' are the OCT optical system, the fundus observation optical system, and the anterior eye observation optical system, respectively. In this pattern, the first dichroic mirror 102 is disposed between the objective lens 101-1 and the OCT optical system on the optical path A', and the optical path A' is the reflection optical path of the first dichroic mirror 102. In this case, the optical path A' is an optical path formed via a single dichroic mirror without an intervention of the second dichroic mirror 103, and therefore achieves high light use efficiency compared to the optical paths B' and C'. Further, the optical path A' is not affected by transmission through the first dichroic mirror 102, whereby it is possible to reduce an astigmatism thereof. As a result, it is possible to acquire a tomographic image having a high brightness and a high contrast on the optical path A'. Further, in the anterior eye observation optical system disposed on the optical path C', it is possible to reduce an astigmatism as described above, whereby it is possible to acquire an anterior eye observation image having a high brightness and a high contrast.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An ophthalmic apparatus comprising:
a holed mirror having an opening part and a mirror part;
a fundus observation optical system that includes a light source for fundus observation, the light source being used for illuminating a fundus of a subject's eye via the holed mirror and an objective lens, and that is configured to obtain a front image of the fundus;
an optical coherence tomography (OCT) optical system for obtaining, using a technique of an optical coherence, a tomographic image of the fundus via the objective lens;
an anterior eye observation optical system for observing an anterior eye observation image of the subject's eye illuminated, via the objective lens with an anterior eye illumination light source;
a first wavelength separation unit disposed between the objective lens and the holed mirror and configured to set a first optical axis of the fundus observation optical system to be coaxial with a second optical axis commonly shared by the OCT optical system and the anterior eye observation optical system; and
a second wavelength separation unit configured to set the optical axis of the OCT optical system to be coaxial with the optical axis of the anterior eye observation optical system to form the second optical axis.

2. The ophthalmic apparatus according to claim 1,
wherein a light source for emitting light having a central wavelength $\lambda$ from approximately 805 nm to approximately 905 nm is used as a measurement light source of the OCT optical system,
wherein a light source for emitting light having a central wavelength $\lambda$ of approximately 970 nm is used as the anterior eye illumination light source,
wherein a light source for emitting light having a central wavelength $\lambda$ of approximately 780 nm is used as the light source for the fundus observation, and
wherein the first wavelength separation unit has a wavelength characteristic of at least light from the light source for the fundus observation and enabling the first wavelength separation unit to reflect light from the measurement light source and light from the anterior eye illumination light source.

3. The ophthalmic apparatus according to claim 1,
wherein a light source for emitting light having a central wavelength $\lambda$ of approximately 970 nm is used as the anterior eye illumination light source,
wherein a light source for emitting light having a central wavelength $\lambda$ of approximately 780 nm is used as the light source for the fundus observation, and
wherein the first wavelength separation unit has a wavelength characteristic allowing the first wavelength separation unit to be transmitted by light from the light source for the fundus observation and enabling the first wavelength separation unit to reflect light from a measurement light source of the OCT optical system and light from the anterior eye illumination light source.

4. The ophthalmic apparatus according to claim 1,
wherein the first wavelength separation unit has a wavelength separation characteristic of transmitting light from the light source for the fundus observation and of reflecting light from the measurement light source and light from the anterior eye illumination light source, and wherein the second wavelength separation unit has a wavelength separation characteristic of transmitting the light from the measurement light source and of reflecting the light from the anterior eye illumination light source.

5. The ophthalmic apparatus according to claim 1, wherein the first wavelength separation unit has a wavelength separation characteristic of transmitting light from the light source for the fundus observation and of reflecting light from the measurement light source and light from the anterior eye illumination light source, and wherein the second wavelength separation unit has a wavelength separation characteristic of reflecting the light from the measurement light source and of transmitting the light from the anterior eye illumination light source.

6. The ophthalmic apparatus according to claim 1, wherein the first wavelength separation unit has a wavelength separation characteristic of reflecting light from the light source for the fundus observation and of transmitting light from the measurement light source and light from the anterior eye illumination light source, and wherein the second wavelength separation unit has a wavelength separation characteristic of transmitting the light from the measurement light source and of reflecting the light from the anterior eye illumination light source.

7. The ophthalmic apparatus according to claim 1, wherein the first wavelength separation unit has a wavelength separation characteristic of reflecting light from the light source for the fundus observation and of transmitting light from the measurement light source and light from the anterior eye illumination light source, and wherein the second wavelength separation unit has a wavelength separation characteristic of reflecting the light from the measurement light source and of transmitting the light from the anterior eye illumination light source.

8. The ophthalmic apparatus according to claim 1, wherein light from the light source for fundus observation has a wavelength of 780 nm, and wherein a light source of the OCT optical system is configured to emit light having a central wavelength longer than the wavelength of the light from the light source for fundus observation and a wavelength bandwidth of approximately 100 nm.

9. The ophthalmic apparatus according to claim 1, further comprising:
a division unit configured to divide light from a light source of the OCT optical system into measurement light and reference light;
a scanning unit disposed on an optical path of the measurement light and configured to scan the fundus of the subject's eye with the measurement light;
a focusing unit disposed between the division unit and the scanning unit on the optical path of the measurement light; and
a driving unit configured to drive the focusing unit along the optical path of the measurement light.

10. The ophthalmic apparatus according to claim 9, wherein a diameter of the measurement light is shorter than a diameter of the light from the light source for fundus observation.

11. The ophthalmic apparatus according to claim 1, further comprising:
an observation scanning unit disposed on an optical path of the fundus observation optical system and configured to scan the fundus with illumination light; and
a light source for visual fixation disposed on the optical path of the fundus observation optical system and closer to the light source for fundus observation than the observation scanning unit is,
wherein the observation scanning unit is used as a scanning unit for visual fixation.

12. An ophthalmic apparatus comprising:
a holed mirror having an opening part and a mirror part;
a fundus observation optical system that includes a light source for fundus observation, the light source being used for illuminating, a fundus of a subject's eye via the holed mirror and an objective lens, and that is configured to obtain a front image of the fundus;
an optical coherence tomography (OCT) optical system for obtaining, using a technique of an optical coherence, a tomographic image of the fundus via the objective lens;
an anterior eye observation optical system for observing an anterior eye observation image of the subject's eye illuminated, via the objective lens with an anterior eye illumination light source;
a first wavelength separation unit disposed between the objective lens and the holed mirror and configured to perform wavelength separation on an optical path of the fundus observation optical system and an optical path commonly shared by the OCT optical system and the anterior eye observation optical system; and
a second wavelength separation unit configured to perform wavelength separation on the optical path of the OCT optical system and the optical path of the anterior eye observation optical system.

13. The ophthalmic apparatus according to claim 12, wherein a light source for emitting light having a central wavelength λ from approximately 805 nm to approximately 905 nm is used as a measurement light source of the OCT optical system, wherein a light source for emitting light having a central wavelength λ of approximately 970 nm is used as the anterior eye illumination light source, wherein a light source for emitting light having a central wavelength λ of approximately 780 nm is used as the light source for the fundus observation, and wherein the first wavelength separation unit has a wavelength characteristic of at least light from the light source for the fundus observation and enabling the first wavelength separation unit to reflect light from the measurement light source and light from the anterior eye illumination light source.

14. The ophthalmic apparatus according to claim 12, wherein a light source for emitting light having a central wavelength λ of approximately 970 nm is used as the anterior eye illumination light source, wherein a light source for emitting light having a central wavelength λ of approximately 780 nm is used as the light source for the fundus observation, and wherein the first wavelength separation unit has a wavelength characteristic allowing the first wavelength separation unit to be transmitted by light from the light source for the fundus observation and enabling the first wavelength separation unit to reflect light from a measurement light source of the OCT optical system and light from the anterior eye illumination light source.

15. The ophthalmic apparatus according to claim 12, wherein the first wavelength separation unit has a wavelength separation characteristic of transmitting light from the light source for the fundus observation and of reflecting light from the measurement light source and light from the anterior eye illumination light source, and
wherein the second wavelength separation unit has a wavelength separation characteristic of transmitting the light from the measurement light source and of reflecting the light from the anterior eye illumination light source.

16. The ophthalmic apparatus according to claim 12, wherein the first wavelength separation unit has a wavelength separation characteristic of transmitting light from the light source for the fundus observation and of reflecting light from the measurement light source and light from the anterior eye illumination light source, and
wherein the second wavelength separation unit has a wavelength separation characteristic of reflecting the light from the measurement light source and of transmitting the light from the anterior eye illumination light source.

17. The ophthalmic apparatus according to claim 12, wherein the first wavelength separation unit has a wavelength separation characteristic of reflecting light from the light source for the fundus observation and of transmitting light from the measurement light source and light from the anterior eye illumination light source, and
wherein the second wavelength separation unit has a wavelength separation characteristic of transmitting the light from the measurement light source and of reflecting the light from the anterior eye illumination light source.

18. The ophthalmic apparatus according to claim 12, wherein the first wavelength separation unit has a wavelength separation characteristic of reflecting light from the light source for the fundus observation and of transmitting light from the measurement light source and light from the anterior eye illumination light source, and
wherein the second wavelength separation unit has a wavelength separation characteristic of reflecting the light from the measurement light source and of transmitting the light from the anterior eye illumination light source.

19. The ophthalmic apparatus according to claim 12, wherein light from the light source for fundus observation has a wavelength of 780 nm, and
wherein a light source of the OCT optical system is configured to emit light having a central wavelength longer than the wavelength of the light from the light source for fundus observation and a wavelength bandwidth of approximately 100 nm.

20. The ophthalmic apparatus according to claim 12, further comprising:
a division unit configured to divide light from a light source of the OCT optical system into measurement light and reference light;
a scanning unit disposed on an optical path of the measurement light and configured to scan the fundus of the subject's eye with the measurement light;
a focusing unit disposed between the division unit and the scanning unit on the optical path of the measurement light; and
a driving unit configured to drive the focusing unit along the optical path of the measurement light.

21. The ophthalmic apparatus according to claim 20, wherein a diameter of the measurement light is shorter than a diameter of the light from the light source for fundus observation.

22. The ophthalmic apparatus according to claim 12, further comprising:
an observation scanning unit disposed on an optical path of the fundus observation optical system and configured to scan the fundus with illumination light; and
a light source for visual fixation disposed on the optical path of the fundus observation optical system and closer to the light source for fundus observation than the observation scanning unit is,
wherein the observation scanning unit is used as a scanning unit for visual fixation.

\* \* \* \* \*